(12) United States Patent
Becher et al.

(10) Patent No.: US 10,184,838 B2
(45) Date of Patent: Jan. 22, 2019

(54) DEVICE AND METHOD FOR DETERMINING THE TEMPERATURE OF A ROAD BUILDING MATERIAL APPLIED BY A CONSTRUCTION MACHINE, AND CONSTRUCTION MACHINE COMPRISING SUCH A DEVICE

(71) Applicant: MOBA Mobile Automation AG, Limburg (DE)

(72) Inventors: Dominik Becher, Limburg (DE); Marcus Watermann, Limburg (DE); David Shelstad, Limburg (DE)

(73) Assignee: MOBA MOBILE AUTOMATION AG, Limburg (DE)

( * ) Notice: Subject to any disclaimer, the term of this patent is extended or adjusted under 35 U.S.C. 154(b) by 0 days.

(21) Appl. No.: 15/583,017

(22) Filed: May 1, 2017

(65) Prior Publication Data
US 2017/0322088 A1 Nov. 9, 2017

(30) Foreign Application Priority Data

May 3, 2016 (DE) .................. 10 2016 207 584

(51) Int. Cl.
*G01J 5/08* (2006.01)
*E01C 19/48* (2006.01)
(Continued)

(52) U.S. Cl.
CPC ............. *G01J 5/089* (2013.01); *E01C 19/48* (2013.01); *E01C 23/01* (2013.01); *G01J 5/026* (2013.01);
(Continued)

(58) Field of Classification Search
CPC ........ F24F 11/30; F24F 11/32; F24F 2120/10; F24F 11/56; F24F 11/52; F24F 2120/12; G01J 5/0025
See application file for complete search history.

(56) References Cited

U.S. PATENT DOCUMENTS 9,476,168 B2 * 10/2016 Oetken ................. E01C 19/002
2008/0260462 A1 * 10/2008 Ackermann .......... E01C 19/288
404/124
(Continued)

FOREIGN PATENT DOCUMENTS

DE 202009016129 U1 * 3/2010 ............ G01J 5/0003
DE 20 2009 016 129 U1 4/2010
(Continued)

OTHER PUBLICATIONS

Quality in clear view Vögele RoadScan, a contactless temperature-measurement system, makes paving quality measurable and verifiable, Apr. 2016 [online], retrieved from the Internet: <http://www.wirtgen-group.com/bauma/en/news/content_projection_article.104789.php>.*

*Primary Examiner* — Christine S Kim
(74) *Attorney, Agent, or Firm* — Keating & Bennett, LLP

(57) ABSTRACT

A device for determining the temperature of a road building material applied by a construction machine in a placement width includes an infrared temperature measuring head, a motor and a controller. The infrared temperature measuring head is arranged to be twistable by the motor in a manner transverse to the direction of travel of the construction machine so as to scan the surface of the road building material to capture temperature measuring values of the surface of road building material during a rotational movement at a plurality of measuring points spaced apart from
(Continued)

one another. The controller is configured to set a scanning speed as a function of a position of the measuring point.

18 Claims, 13 Drawing Sheets

(51) Int. Cl.
*G01J 5/04* (2006.01)
*E01C 23/01* (2006.01)
*G01J 5/02* (2006.01)
*G01N 33/42* (2006.01)

(52) U.S. Cl.
CPC ............... *G01J 5/041* (2013.01); *G01J 5/047* (2013.01); *G01N 33/42* (2013.01)

(56) References Cited

U.S. PATENT DOCUMENTS

| | | | | |
|---|---|---|---|---|
| 2009/0142133 A1* | 6/2009 | Glee | ................... | E01C 19/004 404/75 |
| 2016/0042235 A1* | 2/2016 | Buschmann | .......... | G06T 7/0004 348/148 |
| 2016/0131633 A1 | 5/2016 | Schoenbach et al. | | |

FOREIGN PATENT DOCUMENTS

| | | |
|---|---|---|
| DE | 20 2013 001 597 U1 | 6/2013 |
| DE | 10 2014 222 693 A1 | 5/2016 |
| WO | 00/70150 A1 | 11/2000 |

\* cited by examiner

| dynamic measuring time ||||||
|---|---|---|---|---|---|
| scanning width / cm | | 1000 | scanning width / cm | | 200 |
| position / cm | angle / ° | measuring time / ms | position / cm | angle / ° | measuring time / ms |
| 500 | 63.5 | 74 | 100 | 21.9 | 26 |
| 475 | 62.3 | 66 | 75 | 16.8 | 16 |
| 450 | 61 | 58 | 50 | 11.4 | 10 |
| 425 | 59.6 | 50 | 25 | 5.8 | 6 |
| 400 | 58.1 | 42 | 0 | 0 | 4 |
| 375 | 56.4 | 36 | -25 | -5.8 | 6 |
| 350 | 54.5 | 30 | -50 | -11.4 | 10 |
| 325 | 52.5 | 26 | -75 | -16.8 | 16 |
| 300 | 50.3 | 20 | -100 | -21.9 | 26 |
| 275 | 47.8 | 16 | | | |
| 250 | 45.5 | 12 | | total | 120 |
| 225 | 42.1 | 10 | | | |
| 200 | 38.7 | 8 | | | |
| 175 | 35.1 | 6 | | | |
| 150 | 31.1 | 4 | | | |
| 125 | 26.6 | 4 | | | |
| 100 | 21.9 | 4 | | | |
| 75 | 16.8 | 4 | | | |
| 50 | 11.4 | 4 | | | |
| 25 | 5.8 | 4 | | | |
| 0 | 0 | 4 | | | |
| -25 | -5.8 | 4 | | | |
| -50 | -11.4 | 4 | | | |
| -75 | -16.8 | 4 | | | |
| -100 | -21.9 | 4 | | | |
| -125 | -26.6 | 4 | | | |
| -150 | -31.1 | 4 | | | |
| -175 | -35.1 | 6 | | | |
| -200 | -38.7 | 8 | | | |
| -225 | -42.1 | 10 | | | |
| -250 | -45.5 | 12 | | | |
| -275 | -47.8 | 16 | | | |
| -300 | -50.3 | 20 | | | |
| -325 | -52.5 | 26 | | | |
| -350 | -54.5 | 30 | | | |
| -375 | -56.4 | 36 | | | |
| -400 | -58.1 | 42 | | | |
| -425 | -59.6 | 50 | | | |
| -450 | -61 | 58 | | | |
| -475 | -62.3 | 66 | | | |
| -500 | -63.5 | 74 | | | |
| | total | 960 | | | |

Fig. 4(a)

| static measuring time [20 ms] | | | | | |
|---|---|---|---|---|---|
| scanning width / cm | | 1000 | scanning width / cm | | 200 |
| position / cm | angle / ° | measuring time / ms | position / cm | angle / ° | measuring time / ms |
| 500 | 63.5 | 20 | 100 | 21.9 | 20 |
| 475 | 62.3 | 20 | 75 | 16.8 | 20 |
| 450 | 61 | 20 | 50 | 11.4 | 20 |
| 425 | 59.6 | 20 | 25 | 5.8 | 20 |
| 400 | 58.1 | 20 | 0 | 0 | 20 |
| 375 | 56.4 | 20 | -25 | -5.8 | 20 |
| 350 | 54.5 | 20 | -50 | -11.4 | 20 |
| 325 | 52.5 | 20 | -75 | -16.8 | 20 |
| 300 | 50.3 | 20 | -100 | -21.9 | 20 |
| 275 | 47.8 | 20 | | | |
| 250 | 45.5 | 20 | | total | 180 |
| 225 | 42.1 | 20 | | | |
| 200 | 38.7 | 20 | | | |
| 175 | 35.1 | 20 | | | |
| 150 | 31.1 | 20 | | | |
| 125 | 26.6 | 20 | | | |
| 100 | 21.9 | 20 | | | |
| 75 | 16.8 | 20 | | | |
| 50 | 11.4 | 20 | | | |
| 25 | 5.8 | 20 | | | |
| 0 | 0 | 20 | | | |
| -25 | -5.8 | 20 | | | |
| -50 | -11.4 | 20 | | | |
| -75 | -16.8 | 20 | | | |
| -100 | -21.9 | 20 | | | |
| -125 | -26.6 | 20 | | | |
| -150 | -31.1 | 20 | | | |
| -175 | -35.1 | 20 | | | |
| -200 | -38.7 | 20 | | | |
| -225 | -42.1 | 20 | | | |
| -250 | -45.5 | 20 | | | |
| -275 | -47.8 | 20 | | | |
| -300 | -50.3 | 20 | | | |
| -325 | -52.5 | 20 | | | |
| -350 | -54.5 | 20 | | | |
| -375 | -56.4 | 20 | | | |
| -400 | -58.1 | 20 | | | |
| -425 | -59.6 | 20 | | | |
| -450 | -61 | 20 | | | |
| -475 | -62.3 | 20 | | | |
| -500 | -63.5 | 20 | | | |
| | total | 820 | | | |

Fig. 4(b)

DEVICE AND METHOD FOR DETERMINING THE TEMPERATURE OF A ROAD BUILDING MATERIAL APPLIED BY A CONSTRUCTION MACHINE, AND CONSTRUCTION MACHINE COMPRISING SUCH A DEVICE

CROSS-REFERENCE TO RELATED APPLICATIONS

This application claims priority from German Patent Application No. 102016207584.5, which was filed on May 3, 2016, and is incorporated herein in its entirety by reference.

The present invention relates to the field of construction machines, in particular to a device for determining the temperature of a road building material, such as asphalt, bitumen, asphalt blend material or the like, newly applied by a construction machine, in particular a road finishing machine, in a mounting, or placement, width, the device being arranged at the construction machine in an area within the placement width and the device comprising an infrared temperature measuring head, a motor and a controller, the infrared temperature measuring head being arranged to be twistable, by the motor, in a manner transverse to the direction of travel of the construction machine, and being effective to capture temperature measuring values of the surface of the road building material during a rotational movement at at least two measuring points spaced apart from one another.

Furthermore, the present invention relates to a construction machine comprising such a device.

BACKGROUND OF THE INVENTION

With road building projects, such as building a new road or renewing damaged road surfaces, the quality of the newly applied road building material is to be documented by the executing companies using check tests. Measuring the temperature of the asphalt layer directly after being mounted by the road finishing machine is among these tests. The temperature of the newly applied road building material is measured over the entire placement width directly behind the asphalt plank of the road finishing machine.

A roadway temperature monitoring system comprising a temperature sensor is known from WO 00/70150 A1. The temperature sensor here may either by a thermal-imaging camera, a thermal scanner or a thermal-imaging camera operating in a "line scan" mode. The temperature sensor is arranged at the back end of a road finishing machine such that the entire width of the newly applied asphalt layer is scanned. The captured temperature values may be displayed graphically on a display device.

Disadvantageous with such a temperature sensor is the fact that a thermal-imaging camera or thermal scanner is usually very expensive to buy. In particular, for smaller building companies such an investment usually cannot be realized due to the high costs. Furthermore, it is disadvantageous that the detection or opening angles of a thermal-imaging camera or a thermal scanner are highly limited such that, with mounting, or placement, widths in a range of 8 to 12 meters, for example, a correspondingly adapted objective lens has to be applied at the thermal-imaging camera in order to be able to detect the entire placement width of the newly applied road building material. This, in turn, increases the cost of such a temperature sensor further. Alternatively, both the thermal-imaging camera and the thermal scanner would have to be applied in a correspondingly elevated position at the road finishing machine, i.e. a lot more than four meters above the surface of the newly applied road building material, in order to be able to detect the entire placement width of the newly applied road building material. However, this is of particular disadvantage when passing below bridges.

However, when mounting the thermal-imaging camera or thermal scanner at the road finishing machine in an advantageous area of 3 to 4 meters above the surface of the newly applied road construction material, due to the limited detection or opening angle, a correspondingly flat assembly angle relative to the surface of the newly applied road building material may be employed (cf. FIG. 2, assembly angle $\gamma_F$ may be large) in order for the entire placement width of the newly applied road building material to be detected. However, the temperature of the newly applied road building material over the entire placement width is not measured directly behind the asphalt plank of the road finishing machine but in a correspondingly large distance to the back edge of the asphalt plank. Consequently, the temperature values measured no longer correspond to the actual values in the area directly behind the asphalt plank.

A device, as described above, for measuring the temperature of the surface of hot asphalt, including an infrared temperature measuring head moving transverse to the direction of travel, a motor for moving this sensor and a controller, is known already from DE 20 2009 016 129 U1.

Based on this device, calculating the placement width of the newly applied asphalt layer is known from DE 20 2013 001 597 U1. Same is calculated using the height of the measuring head above the asphalt layer, which is determined using a distance sensor, and the angle values where the measuring head changes its direction of movement.

When capturing the temperature measuring values by means of the known device, however, the result is not a steady measuring point pattern. As the assembly position and/or the assembly angles of the device change, so does the distance between the measuring points on the surface of the newly applied road building material. In addition, the distance between the measuring points in the direction of travel of the construction machine changes with a changing speed of travel of the construction machine. If same moves faster, the distance between the measuring points in the direction of travel will become larger.

Post-published DE 10 2014 222 693 A1 describes a device for determining the temperature of a road building material applied at a placement width by a construction machine, said device being arranged on the construction machine in the area within the placement width and comprising an infrared temperature measuring head, a motor and a controller. The infrared temperature measuring head is arranged to be twistable by the motor in a direction transverse to the direction of travel of the construction machine, and is effective to capture, during a rotational movement temperature measuring values of the surface of the road building material at at least two measuring points spaced apart from one another. The controller is effective to control the motor, on the basis of the mounting position of the device on the construction machine, such that the distance between the measuring points on the surface to be measured remains the same.

Temperature measurements performed by means of a temperature scanner known from conventional technology are less precise in the area of the asphalt edges, or roadway edges, e.g. to the left and to the right and/or in the area of the end of the plank or of the outer edge of the plank, than they are within the central area, e.g. in the area of the center of the plank. In the temperature scanners known from conventional technology, the asphalt surface temperature is determined by means of a constant dwell time for measurement in that the scanner is stopped at every measuring point. The dwell time is approx. 10 ms or 20 ms, for example. As is described in DE 10 2014 222 693 A1, for example, the time constant is adjustable.

SUMMARY

According to an embodiment, a device for determining the temperature of a road building material applied by a construction machine in a placement width may have: an infrared temperature measuring head, a motor, and a controller, wherein the infrared temperature measuring head is arranged to be twistable, by the motor, in a manner transverse to the direction of travel of the construction machine to scan the surface of the road building material so as to capture temperature measuring values of the surface of the road building material during a rotational movement at a plurality of measuring points spaced apart from one another, wherein the controller is configured to set a scanning speed as a function of a position of the measuring point.

According to another embodiment, a construction machine may have at least one inventive device, said device being arranged in the back area and/or in the front area of the construction machine.

According to another embodiment, a method of determining the temperature of a road building material applied by a construction machine in a placement width may have the steps of: scanning the surface of the road building material by twisting an infrared temperature measuring head in a direction transverse to the direction of travel of the construction machine, and capturing, by the infrared temperature measuring head, of temperature measuring values of the surface of the road building material at a plurality of measuring points spaced apart from one another, wherein a scanning speed at which the infrared temperature measuring head scans a measuring point is set as a function of a position of the measuring point.

In accordance with embodiments, the controller is configured to set the scanning speed as a function of an angle by which the infrared temperature measuring head is twisted in relation to a perpendicular to the surface.

In accordance with embodiments, the controller is configured to reduce the scanning speed as the angle increases, and to increase the scanning speed as the angle decreases.

In accordance with embodiments, the scanning speed is higher, within a first angular range around the perpendicular to the surface, than is the scanning speed within a second angular range outside the first angular range.

In accordance with embodiments, the scanning speed within a first angular range around the perpendicular to the surface has a first value, and the scanning speed within a second angular range and within a third angular range, which span the first angular range and the first and/or second edge of the surface, has a second value lower than the first value.

In accordance with embodiments, the controller is configured to control the motor such that the infrared temperature measuring head is oriented toward a measuring point in order to capture a temperature measuring value of said measuring point during a dwell time, the controller being configured to set the dwell time as a function of a position of the measuring point along the width of the surface.

One advantage of the invention is in the increase of the accuracy of measurement in the area of the asphalt edges and/or roadway edges in that a longer stop of the scanner is caused, i.e. the time duration for a measurement is increased, within said area, e.g. within the area of the lateral asphalt edges. In other words, the speed of the scanner is varied during the movement from the left to the right (or from one side to the other). As compared with a central area, e.g. in the area of the center of the plank, the twisting angle of the scanner in relation to the horizontal is large in said area, and less heat radiation (radiation energy) is reflected onto the sensor by the newly applied road surface. The accuracy of measurement increases as the duration of the measurement at the measuring point increases. In the central area of the roadway, e.g. in the area of the center of the plank, scanning may be performed more quickly, i.e. the stop times of the scanner are shorter since the twisting angle of the scanner in relation to the horizontal is smaller and since, therefore, more heat radiation (radiation energy) is reflected onto the sensor.

In addition to an increase in the accuracy of measurement, a further advantage of the invention is that, as compared to a constant dwell time, more measuring points, e.g. a smaller distance between measuring points, may be selected within an identical time frame, whereby increased resolution of the measurement system is achieved. Alternatively, the total scan time of a scan process (from one side to the other) may be reduced while the number of measuring points stays the same, as a result of which more scans may be performed and, thus, a higher level of resolution is achieved.

A dynamic measuring time, e.g. a varying measuring time which increases in a linear, stepwise or exponential manner, for example, of the scanner leads to time savings, e.g. with narrow roads, e.g. a sidewalk, cycle path or the like, since more measurements are possible during the same amount of time as compared to a constant measuring time. As a result, the level of resolution of the measuring system also increases. In the event of broad roads, e.g. motorways, there may actually be a slight increase in the duration of measurement, but the level of accuracy in the area of the asphalt edges and/or roadway edges will be increased, which is not achieved in the event of the measuring time being constant.

Further embodiments of the present invention provide a device wherein the controller is effective to control, when assembling the device on the construction machine in the area within the placement width (B), the motor based on the assembly position of the device on the construction machine such that the distance between the measuring points on the surface to be measured remains steady.

In accordance with embodiments, the controller is effective to control the motor additionally based on the assembly angles of the device on the construction machine.

Thus, a predetermined or preset distance of 25 cm, for example, between two measuring points transverse to the direction of travel of the construction machine is maintained on the surface of the newly applied road building material over the entire placement width, irrespective of the assembly position and the assembly angles of the device. When the assembly position and/or assembly angles of the device are changed, exemplarily when rebuilding a tool at the machine, i.e. the device is shifted in height and/or transverse to the direction of travel of the construction machine and/or the assembly angles of the device are changed, the preset distance of 25 cm, for example, between two measuring points transverse to the direction of travel of the construction machine will be maintained over the placement width even after changing the assembly position and/or the assembly angles.

In accordance with embodiments, this is achieved by the fact that, with a changing assembly position and/or changing assembly angles of the device, the motor controller is adapted correspondingly and, thus, the predetermined or set distance between two measuring points transverse to the direction of travel of the construction machine is restored and advantageously kept nearly equal.

Advantageously, the infrared temperature measuring head may be tilted by a very large angle, exemplarily in a range of about 120° to 130°. Thus, it is possible, using the inventive device, to detect temperature measuring values in a large area of a placement width of up to 14 meters directly behind the asphalt plank of a road finishing machine, with an advantageous assembly height of the device in the area of 3 to 4 meters above the surface of the newly applied road building material. The inventive device thus is not limited only to the field of large placement widths, but, due to the variable twisting angle of the infrared temperature measuring head, may be used instead for all the placement widths of a road surface in the area mentioned before. Compared to thermal-imaging cameras or thermal scanners, this is advantageous since these usually comprise a fixed detection or opening angle. In addition, the road finishing machine here may pass below bridges, or the like, without any problem.

Of further advantage are the simple assembly of the device on the construction machine and the moderate costs of the individual components of the device and, correspondingly, the entire device. In particular, an infrared temperature measuring head is many times cheaper compared to a thermal-imaging camera or a thermal scanner. This means that purchasing the inventive device is also affordable for smaller building companies.

Thus, it is possible using the inventive device for a steady number of measuring points to be present for determining the temperature of the newly applied road building material with a steady placement width of the newly applied road building material.

The requirement of having a steady number of measuring points or a steady distance between two measuring points will surely be a topic in biddings for road building projects, exemplarily for building a new road or renewing damaged road surfaces, in order to achieve steady and, thus, comparable quality measurements of the newly applied road building material.

In accordance with embodiments, the speed of movement of the infrared temperature measuring head changes as a function of the speed of travel of the construction machine. This means that an equal distance between the measuring points in the direction of travel of the construction machine, i.e. an equal distance between the series of measurements, is achieved on the surface of the newly applied road building material, irrespective of the speed of travel of the construction machine. When, for example, the distance between the series of measurements, i.e. the measuring points in the direction of travel of the construction machine, is 25 cm, when increasing the speed of travel of the construction machine, the speed of movement of the infrared temperature measuring head has to be increased as well and vice versa.

In order to achieve an approximately steady distance between the series of measurements, the controller for the motor or an evaluating unit arranged at the device or at the construction machine is advantageously connected electrically to the construction machine control computer or a displacement measuring means arranged at the construction machine, such as, for example, a travel wheel which is usually employed in road finishing machines. The speed value achieved in this way may then be used for calculating the speed of movement of the infrared temperature measuring head. Calculating the speed of movement of the infrared temperature measuring head may take place either in the controller for the motor or in the evaluating unit arranged at the device or at the construction machine.

The advantage of adapting the speed of movement of the infrared temperature measuring head to the speed of travel of the construction machine is such that a homogeneous network of measuring points results in connection with an equal measuring point distance transverse to the direction of travel of the construction machine, i.e. in the direction of movement of the infrared temperature measuring head. No more measuring points are captured by the infrared temperature measuring head than may be used for illustrating and taking down the measured temperature measuring value, for example on a control computer and/or a display and operating unit connected thereto. Post-processing the captured temperature measuring value, exemplarily by the control computer, such as discarding or cancelling measuring values or series of measurements no longer required or an interpolation of measuring values or series of measurements, may be omitted. Limiting the quantity of data to be transmitted to a minimum is also of advantage for transmitting the data to different construction machines, such as, for example, a roller, in order to show the data to the roller driver on a display unit in a compressed and simple manner.

Compared to a thermal-imaging camera or a thermal scanner, this is advantageous since these usually exhibit a very high resolution. Usually, many more measuring points are captured than may be used for illustrating and taking down the measured temperature measuring values, exemplarily on a control computer and/or a display and operation unit connected thereto. The result here may be a high quantity of data which has to be processed by the control computer.

In accordance with embodiments, the direction of movement of the infrared temperature measuring head changes as soon as the measured temperature falls below a predetermined minimum value, exemplarily 80° C., at at least one measuring point. The infrared temperature measuring head which is moved by the motor transverse to the direction of travel of the construction machine continually measures the surface temperature of the newly applied road building material. The temperature values are usually in a range of 120 to 170° C., or, in the event of low-temperature asphalt, quite possibly even below that. At positions where temperature values are measured to lie below a specific temperature value (depending on the asphalt material used), e.g. in the range of 80 to 120° C., the road building material mounted has been too cold—a so-called "cold spot" forms in the newly applied road layer, which decreases the temperature of the road surface. However, if the infrared temperature measuring head measures a temperature of less than 80° C., for example, it can be assumed that one of the two outer edges, i.e. the lateral end of the newly applied road layer, has been reached.

It is also possible for a so-called "cold spot" to be in a range below the predetermined minimum value of 80° C., for example. In order to avoid a premature and, possible, erroneous change in the direction of movement of the infrared temperature measuring head in this case, the infrared temperature measuring head is at first moved until the outer edge determined previously has been reached and the captured temperature measuring values of the presently performed series of measurements are compared to the values of at least one of the series of measurements captured before.

If at least one temperature value which is above the predetermined minimum value, i.e. above 80° C., for example, is determined at the measuring points in the edge area of the road surface, i.e. in the area of the outer edges, it can be assumed that the present placement width has not decreased and that a so-called "cold spot" is present in the newly applied road layer. In this case, the infrared temperature measuring head is advantageously moved to the outer edge determined before, or beyond, until a temperature of less than 80° C., for example, is measured at at least one measuring point. In this case, it can be assumed that one of the two outer edges, i.e. the lateral end of the newly applied road layer, has been reached.

If only temperature values below the predetermined minimum value, i.e. below 80° C., for example, are determined at the measuring points in the area of the outer edges, it can be assumed that either the present placement width has decreased or that there is a so-called "cold spot" in the edge area of the road surface, i.e. in the area of the outer edges. The infrared temperature measuring head will advantageously decrease the measuring range in the subsequent series of measurements and thus approximate a changed placement width or outer edge. The infrared temperature measuring head is only twisted until a temperature of less than 80° C., for example, is measured at at least one measuring point. The infrared temperature measuring head then assumes that one of the two outer edges has been reached, i.e. the lateral end of the newly applied road layer.

When decreasing the placement width, the number of measuring points where the infrared temperature measuring head captures measuring values, also decreases due to the equal distance between measuring points. In the opposite case, i.e. when widening the placement width, the number of measuring points will increase correspondingly.

In accordance with embodiments, the position where the infrared temperature measuring head changes its direction of movement is stored in the controller or an evaluating unit arranged at the device or at the construction machine for calculating the placement width of the newly applied road building material. The placement width of the newly applied road building material is than calculated from the stored angular positions of the infrared temperature measuring head and the height and the assembly angles of the device or the infrared temperature measuring head relative to the surface of the newly applied road building material.

In accordance with embodiments, the distance between the measuring points and/or the duration of the temperature measurement at a measuring point may be set. Thus, the distance between two measuring points is set both transverse to the direction of travel of the construction machine and in the direction of travel of the construction machine, advantageously by programming the controller, exemplarily using a control computer or a display and operating unit connected thereto. The time constant of the infrared temperature measuring head, i.e. the duration of the temperature measurement at a measuring point, may also be set, advantageously by programming, exemplarily using a control computer or a display and operating unit connected thereto. It is advantageously possible here to adjust the device to, for example, country-specific requirements. Since, in the US, a new road layer is mounted at a higher speed of travel of the road finishing machine, the duration of the temperature measurement at a measuring point has to be shortened here. Additionally, in the US, the distance between two measuring points is usually about 30 cm, whereas in Germany a measuring point distance of about 25 cm is being forced at present.

In accordance with embodiments, a contactless distance measurer, such as a laser distance measurer, is arranged in the area of the device, by means of which the distance of the infrared temperature measuring head to a measuring point where the infrared temperature measuring head is arranged, in the direction of travel of the construction machine, essentially perpendicularly to the surface of the road building material is measured. Compared to a height measurement by one of the machine operators, exemplarily using a measuring tape, such a distance or range measurement is of advantage since the measured value may be read out on the display and operating unit before beginning the construction works and subsequently be programmed into the controller of the device. Laser sensors operating according to the light run time measurement principle are advantageously used for measuring distances, however, ultrasonic sensors or different sensor technologies may also be used.

In accordance with embodiments, the contactless distance measurer is part of the inventive device. Alternatively, the contactless distance measurer may be an external sensor which is, for example, arranged at a suitable position at the device or at the construction machine and connected to the device.

In accordance with embodiments, the contactless distance measurer is electrically connected to the controller of the device. Compared to manually programming the height value into the controller, exemplarily using a control computer or a display and operating unit connected thereto, it is advantageous for the measured value to be transferred directly from the distance measurer to the controller. Thus, erroneous inputs by one of the machine operators, for example, are avoided.

In accordance with embodiments, the controller is electrically connected to a weather station arranged at the construction machine which exemplarily determines the wind speed, ambient temperature, air humidity, rainfall and/or other ambient parameters in the area of the construction machine. Thus, the weather station transmits the determined measuring values to the controller which, in turn, uses or stores same for further calculations, exemplarily calculating the core temperature of the newly applied road building material.

In accordance with embodiments, the motor is a stepper motor, a servomotor, a direct-current motor or a direct-current motor including a gear unit.

The present invention also provides a construction machine, in particular a road finishing machine, comprising at least one inventive device, the device being arranged in the back area and/or the front area of the construction machine.

BRIEF DESCRIPTION OF THE DRAWINGS

Embodiments of the present invention will be detailed subsequently referring to the appended drawings, in which:

FIG. 4(a) shows two tables which reflect, for a wide road and a narrow road, the inventive variation of the measuring times or durations of measurement (dynamic measuring times) as a function of the position of the point of measurement along the width of a surface newly applied by a road finishing machine;

FIG. 4(b) shows two tables for the wide road and the narrow road of FIG. 4(a), wherein a conventional approach involving a static measuring time was employed;

DETAILED DESCRIPTION OF THE INVENTION

Figure 1:
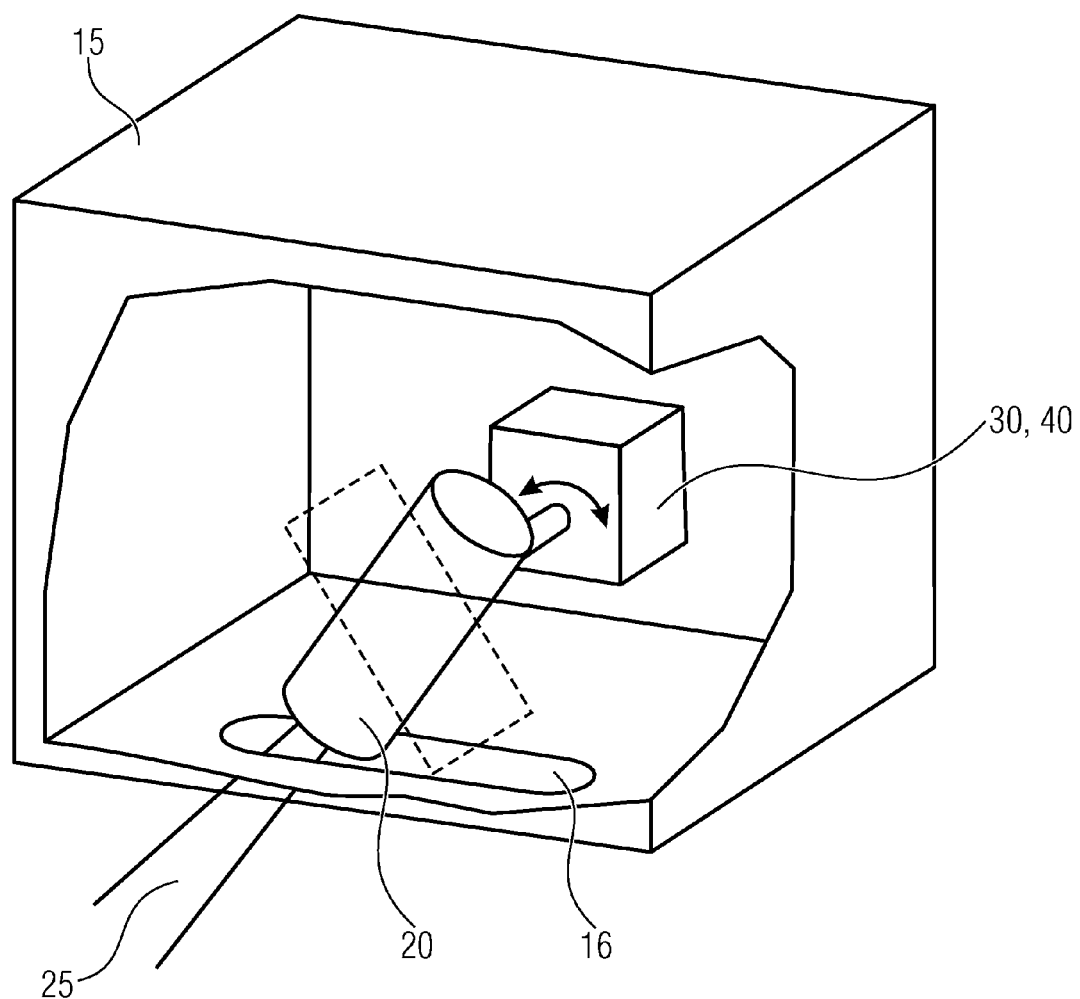
FIG. 1 shows a schematic setup of the inventive device.

In the subsequent description of embodiments, same elements or elements of equal effect will be provided with same reference numerals in the appended drawings.

FIG. 1 schematically illustrates an inventive device which basically consists of a motor 30, an infrared temperature measuring head 20 arranged at the motor 30 or the motor axis, and a controller 40 arranged in the area of the motor 30. All the components mentioned are arranged so as to be protected in a casing 15, the casing 15 comprising an essentially longitudinal opening 16 in its lower area, i.e. in the direction towards the surface 110 of a newly applied road surface (not illustrated here). The fact that the infrared temperature measuring head 20 is arranged at the motor 30 or the motor axis causes the infrared temperature measuring head 20 to be twisted also with a twisting movement of the motor axis. This is indicated schematically in the figure by a broken-line position of the infrared temperature measuring head 20. Advantageously, the infrared temperature measuring head 20 may be twisted within an angular range of about 120° to 130°. During a rotational movement, the infrared temperature measuring head 20 captures temperature measuring values through the opening 16 at at least two measuring points 100 to 103 spaced apart from one another on the surface 110 of the newly applied road surface 20 (see, for example, FIG. 3 and FIG. 7) by means of the infrared radiation 25 emitted from the surface 110.

Figure 2:
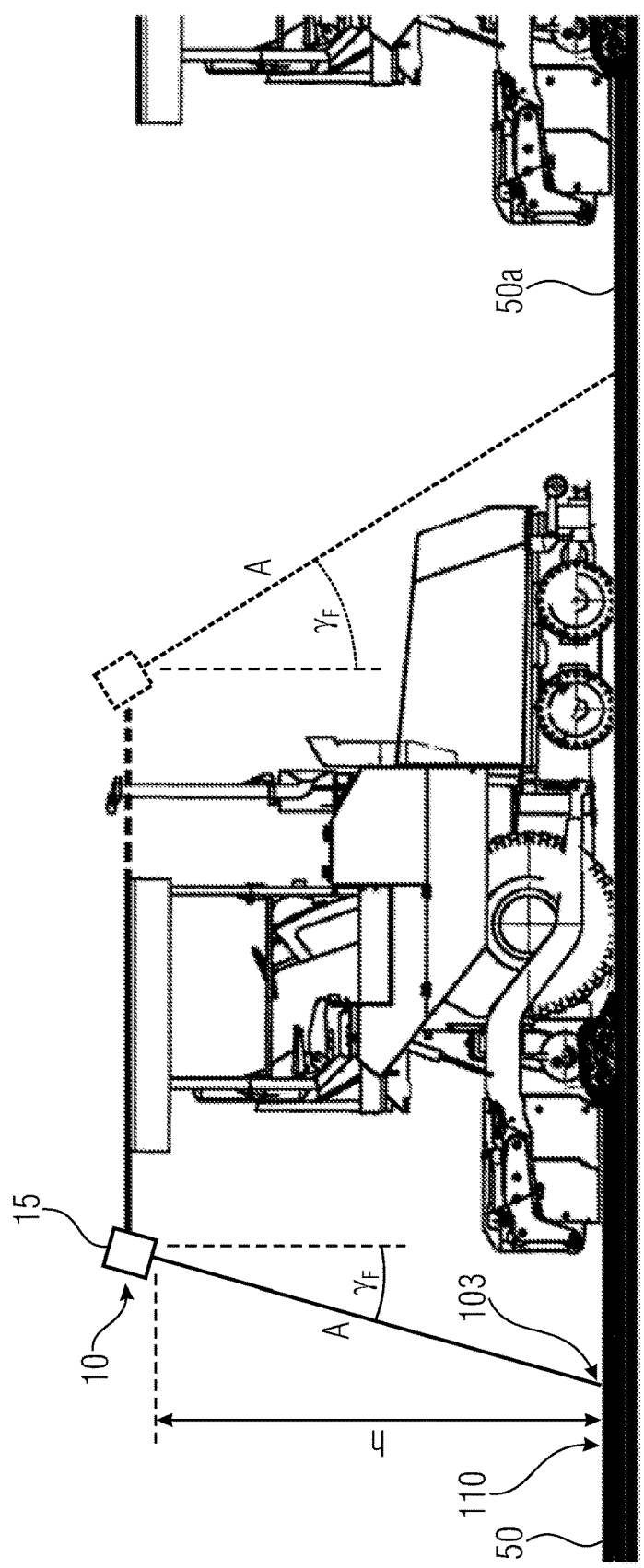
FIG. 2 shows a schematic illustration of a road finishing machine comprising an inventive device each in the front and back areas.

FIG. 2 shows the inventive device which is arranged at a position 10 in the height h to the surface 110 of the newly applied road surface 50 in the back area of a road finishing machine illustrated in side view and also in the front area thereof (illustrated in the figure in broken lines). Usually, the device is assembled only in the back area of the road finishing machine and captures temperature measuring values of the newly applied road surface 50. However, it is also feasible for the device to be mounted only in the front area of the road finishing machine which exemplarily mounts an asphalt cover layer, or in addition in the back area. When assembling the device in the front area of the road finishing machine, temperature measuring values of the ground 50a to be asphalted are captured, irrespective of whether or not a road surface has been mounted before by a different road finishing machine such as, for example, an asphalt binding layer.

As is illustrated in FIG. 2, irrespective of whether it is assembled in the front and/or back area of the road finishing machine, as seen transverse to the direction of travel of the road finishing machine, the device is not arranged at the road finishing machine to be perpendicular to the surface 110, but in an assembly angle $\gamma_F$ in a range of 15° to 30°, for example, relative to a perpendicular line at the road finishing machine. The result is that the distance A schematically illustrated in FIGS. 2 to 10 does not necessarily equal the assembly height h of the device(s) above the surface 110 but that the distance A will be the distance between the device and the measuring point 103 where the infrared temperature measuring head 20 is arranged, in the direction of travel of the construction machine, essentially perpendicularly to the surface 110 of the road building material 50. In order to ensure a measuring precision of +/−3° C., it is advantageous for the infrared temperature measuring head 20 not to be assembled on the road finishing machine beyond a maximum assembly angle $\gamma_F$ of about 45° relative to a perpendicular line.

Figure 3:
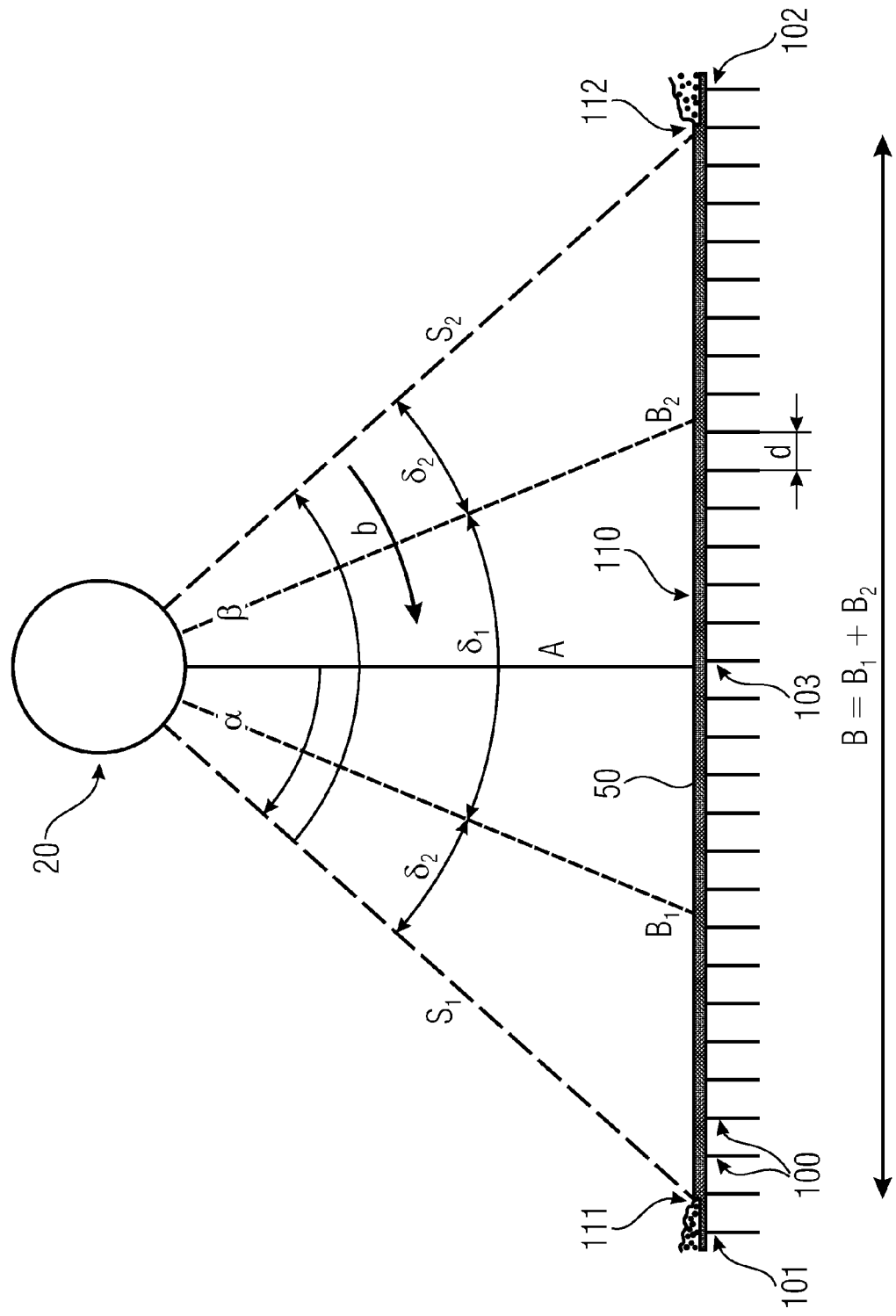
FIG. 3 shows a schematic representation for illustrating the mode of operation of the inventive device with variable measuring times in accordance with an embodiment.
Figure 5A:
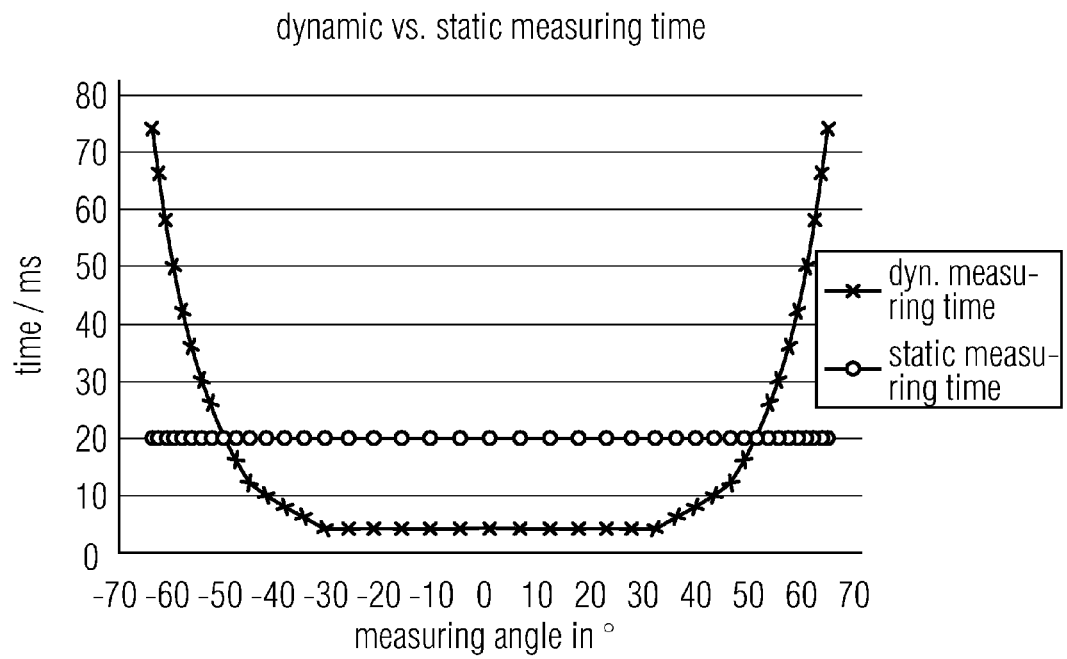
FIG. 5(a) shows the profile of the measuring time across the measuring angle for the wide road.
Figure 5B:
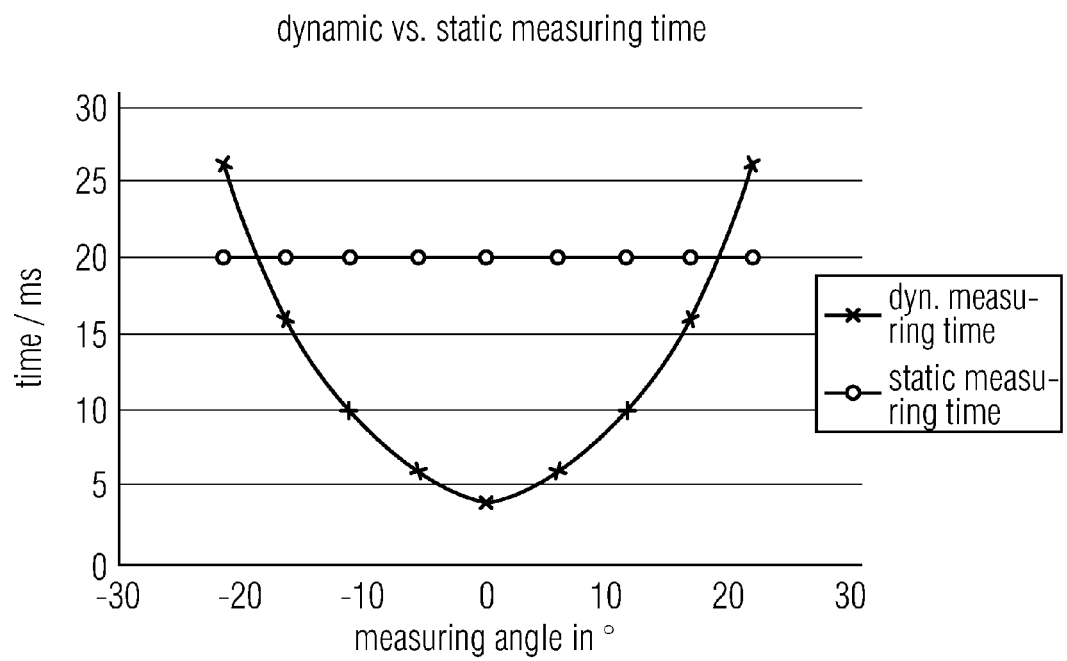
FIG. 5(b) shows the profile of the measuring time across the measuring angle for the narrow road.

FIG. 3 is a schematic representation for illustrating the mode of operation of the inventive device with variable measuring times in accordance with an embodiment. The infrared temperature measuring head 20 illustrated in FIG. 3 moves in the directions of movement indicated by the reference numeral b and captures, while moving, temperature measuring values at the measuring points 100 to 103 illustrated at a distance d on the surface 110 of the newly applied road surface 50. The direction of movement of the infrared temperature measuring head 20 changes as soon as the measured temperature falls below a minimum value of 80° C., for example, at one of the measuring points 101 and 102. Thus, the captured temperature measuring values of the series of measurements performed at present are compared to the values of at least one of the series of measurements captured before in order to avoid a premature and, possibly, erroneous change in the direction of movement of the infrared temperature measuring head 20. The measuring points 101 and 102 are outside the area where the road building material 50 is applied by the road finishing machine. This area is indicated in FIG. 3 by the two outer edges 111 and 112.

The measuring points 100 to 103 are schematically indicated to be short, perpendicular lines arranged below the newly applied road surface 50 at a mutual distance d. The measuring point 103 is the measuring point where the infrared temperature measuring head 20, in the direction of travel of the construction machine, is arranged essentially perpendicularly to the surface 110 of the road building material 50. In addition, in FIGS. 3 to 6, the area which the infrared temperature measuring 20 moves through is indicated by the outer infrared radiation lines $S_1$ and $S_2$. The two angles α and β which each reach from the infrared radiation line $S_1$, $S_2$ to the distance line A, are also defined by this. The controller 40 which controls the motor 30 for twisting the infrared temperature measuring head 20 or an evaluating or calculating unit (not illustrated here) arranged outside the device may calculate the two subsections $B_1$=tan α×A and $B_2$=tan β×A from the two angular values α and β and from the known distance A of the device or infrared temperature measuring head 20 to the surface 110 of the newly applied road surface 50. The overall placement width B will subsequently result from adding the two subsections $B_1$ and $B_2$.

FIG. 3, an area that is scanned by the scanner 20 and is adjacent to the asphalt edges and/or roadway edges 111, 112 is indicated by the angular ranges $δ_2$, and an area around the perpendicular line A, which in the embodiment depicted in FIG. 3 is located halfway between the edges 111, 112, is indicated by the angular range $δ_1$. In order to increase the accuracy of measurement within the angular ranges $δ_2$ adjacent to the asphalt edges and/or roadway edges 111, 112, the time duration of the measurements is increased within the angular ranges $δ_2$. Within the angular ranges $δ_2$, the twisting angle α, β of the scanner in relation to the horizontal is large, so that less heat radiation (radiation energy) is reflected onto the sensor 20 by the newly applied road surface. An increase in the duration of measurement results in an increase in the accuracy of measurement. In the central area (angular range $δ_1$) of the roadway 50, e.g. in the area of the center of the plank, scanning is performed faster, i.e. the stop times of the scanner 20 are shorter. Due to the smaller twisting angle α, β of the scanner 20 in relation to the horizontal, more heat radiation (radiation energy) is reflected onto the sensor 20.

In this embodiment, the scanning speeds are smaller within the angular ranges $δ_2$ than within the angular range $δ_1$. In other embodiments, different measuring times may be employed in different angular ranges, respectively. Alternatively, the measuring times may be reduced in a linear, stepwise or exponential manner in the direction of the edges 111, 112, starting from the perpendicular line A or starting from the angular range $δ_1$ wherein the measuring times may be essentially constant. In further embodiments, the scanned area may be subdivided into more than the three depicted angular ranges.

In accordance with the invention, in other words, the speed of the temperature scanner 20 is thus dynamically changed, or varied, during the movement from the left to the right, or from one side 111 to the other 112. In accordance with embodiments, the dwell time at the respective measuring point is increased toward the outside, starting from the central position 103. Advantageously, this dwell time exponentially increases to approx. 75 ms from an initial approx. 4 ms in the area of the asphalt edges, or roadway edges, 111, 112. Alternatively, the dwell time may also be adapted area by area, e.g. predefined by twisting angle ranges of the scanner 20. For example, with twisting angles ranging from 0 to 15°, the duration of measurement is set to 10 . . . 15 ms, with twisting angles ranging from 16 to 30°, the duration of measurement is set to 25 . . . 30 ms, and with twisting angles ranging from 31 to 55°, the duration of measurement is set to 40 . . . 75 ms.

FIG. 4(a) shows two tables which explain, for two examples, the inventive variation of the measuring times or durations of measurement (dynamic measuring times) as a function of the position of the measuring point along the width of a surface newly applied by a road finishing machine. In the left-hand table, the measuring times are indicated for a "wide road" (width of 10 m, for example a motorway), and in the right-side table, the measuring times are indicated for a "narrow road" (width of 2 m, for example a sidewalk). The length of the measurement beam perpendicular to the surface is 250 cm. For comparative purposes, FIG. 4(b) shows two tables for the two mentioned examples, wherein a conventional approach with a static measuring time of 20 ms was used.

A comparison of FIGS. 4(a) and 4(b) between the constant dwell time/measuring time of the scanner at the measuring point (static measuring time 20 ms—FIG. 4(b)) and the varying dwell time (dynamic measuring time—FIG. 4(a)) shows that the dwell time (measuring time) exponentially increases, in the dynamic variant, from an initial approx. 4 ms to approx. 75 ms (in the area of the asphalt edges, or roadway edges, 111, 112). This exponential increase is depicted for both examples in the illustration of FIGS. 5(a) and 5(b), which indicate, for the above-mentioned examples, the course of the measuring time across the measuring angle, FIG. 5(a) for the wide road, and FIG. 5(b) for the narrow road. For comparative purposes, the course of the measuring time across the measuring angle is also depicted for a constant measuring time in each case. The twisting angle of the scanner is indicated along the X axis, and in FIG. 5(a) one can recognize that in the event of a measurement with a constant measuring time, the differences between successive angles in relation to the asphalt edge become smaller toward the asphalt edge, or in the direction of the roadway edge, so that a constant distance between the measuring points is ensured.

From the comparison of FIGS. 4(a) and 4(b) one may gather that the dynamic measuring time leads to a slight increase in the duration of measurement with wide roads; however, the level of accuracy is increased in the area of the asphalt edges, or roadway edges, which is not achieved when employing constant measuring time. With narrow roads, the varying and exponentially increasing measuring time of the scanner also results in time savings since more measurements are possible within the same amount of time as compared to a constant measuring time. As a result, the level of resolution of the measuring system also increases.

Figure 6:
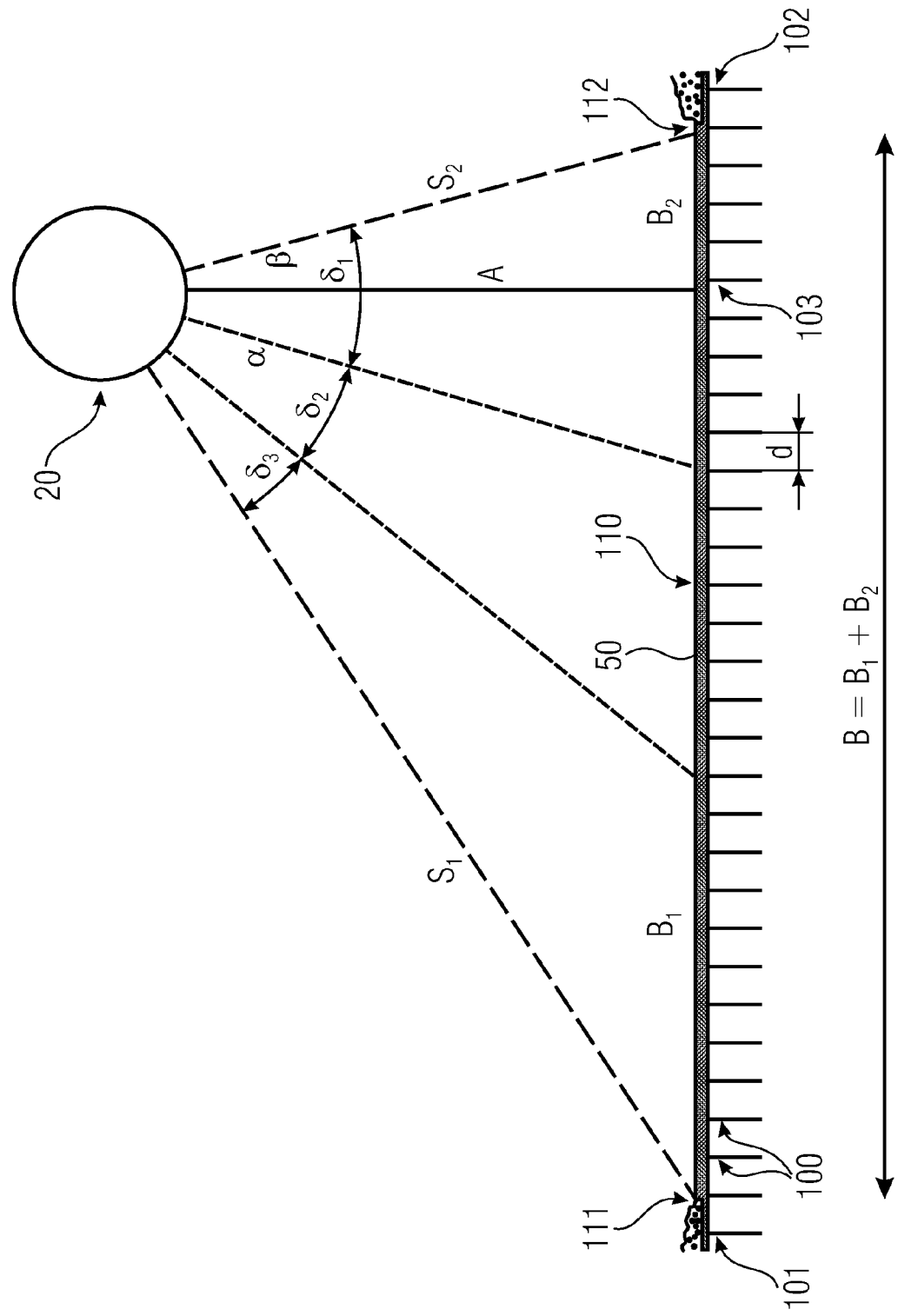
FIG. 6 shows a schematic illustration of the mode of operation illustrated in FIG. 3, however with a device arranged to be offset to the right relative to the direction of travel of the construction machine.

In FIG. 3, the device is arranged in an essentially central manner and in a manner that is transverse to the direction of travel of the construction machine (not depicted here). In other embodiments, the position of the device on the road finisher is different. FIG. 6 shows an embodiment wherein the device is arranged to be offset to the right in relation to the direction of travel of the road finisher. In this embodiment, the scan speeds are increasingly reduced within the three depicted angular ranges $δ_1$, $δ_2$, and $δ_3$, starting from the angular range $δ_1$. Alternatively, the measuring times within the angular range $δ_1$ may be constant and may be reduced in a linear, stepwise or exponential manner in the direction toward the edge 111. In further embodiments, the scan range may be subdivided into more than the depicted three angular ranges.

Further embodiments of the present invention will be described below wherein the controller is effective to control the motor, during assembly of the device on the construction machine in the area within the placement width (B), on the basis of the assembly position of the device on the construction machine, such that the distance of the measuring points on the surface to be measured remains the same.

Figure 7:
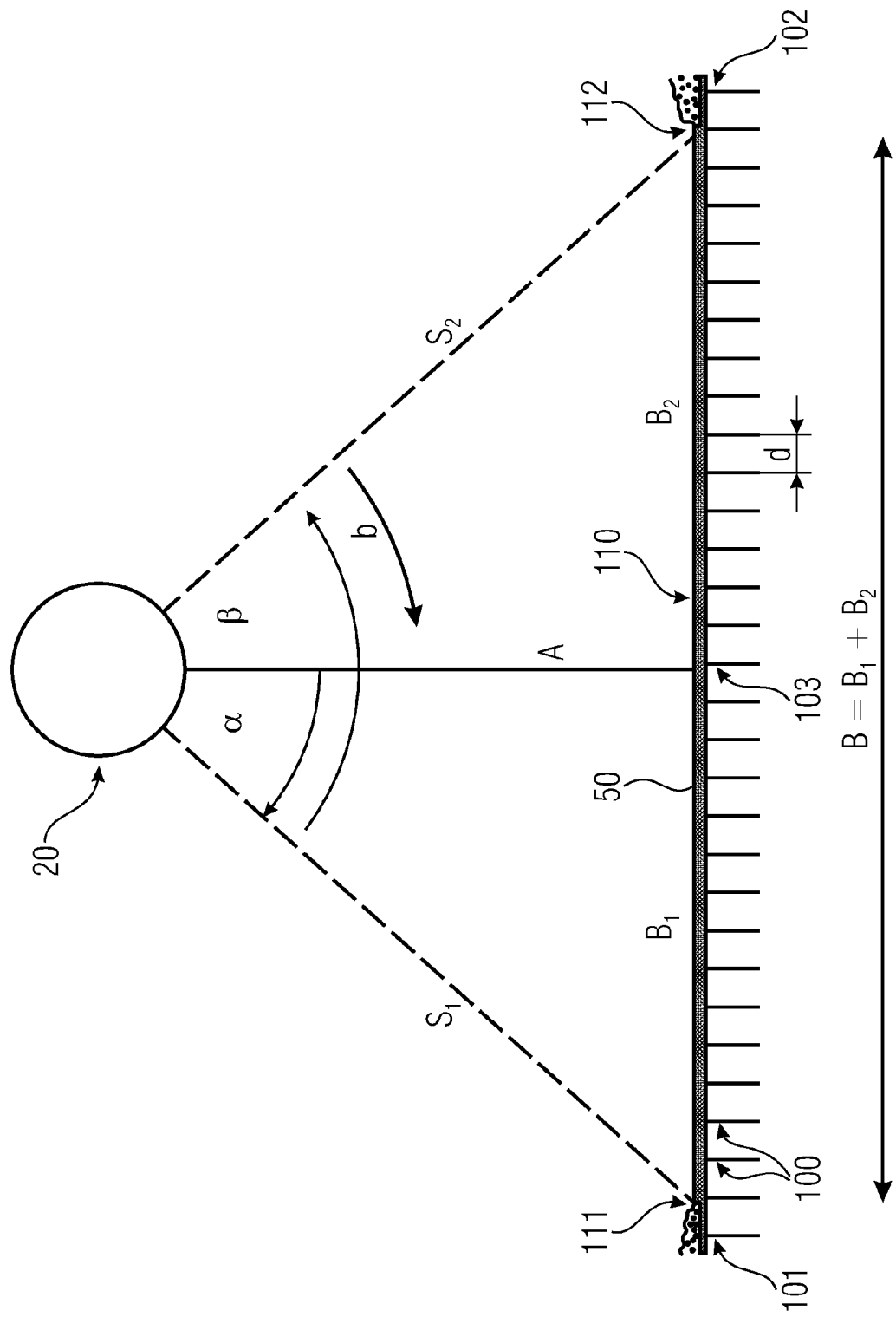
FIG. 7 shows a schematic representation for illustrating the mode of operation of the inventive device for maintaining constant distances between the measuring points in accordance with a further embodiment.

The infrared temperature measuring head 20 depicted in FIG. 7 moves in the directions of movement indicated by reference numeral b and captures, during the movements, temperature measuring values at the measuring points 100 to 103, depicted at a distance d, on the surface 110 of the newly applied road surface 50. The direction of movement of the infrared temperature measuring head 20 changes as soon as the temperature measured falls below a minimum value of e.g. 80° C. at any of the measuring points 101 and 102. To this end, the captured temperature measuring values of the currently performed series of measurement are compared to the values of at least one of the previously captured series of measurements so as to avoid premature and possibly erroneous change in the direction of movement of the infrared temperature measuring head 20. The measuring points 101 and 102 are located outside the area where the road building material 50 is applied by the road finishing machine. This area is indicated by the two outer edges 111 and 112 in FIGS. 7 to 12.

All of the measuring points 100 to 103 are schematically depicted to be short, perpendicular lines below the newly applied road surface 50 which are arranged at a mutual distance d. The measuring point 103 is that measuring point at which the infrared temperature measuring head 20 is arranged essentially perpendicularly to the surface 110 of the road building material 50 in the direction of travel of the construction machine. In addition, in FIGS. 7 to 10, that area wherein the infrared temperature measuring head 20 is moving is indicated by the two outer infrared radiation lines $S_1$ and $S_2$. In this manner, the two angles $\alpha$ and $\beta$ are also defined, which span the infrared radiation line $S_1$, $S_2$ and the distance line A, respectively. From the two angular values $\alpha$ and $\beta$ as well as from the known distance A between the device, or infrared temperature measuring head 20, and the surface 110 of the newly applied road surface 50, the controller 40, which controls the motor 30 to twist the infrared temperature measuring head 20, or an evaluation and/or calculation unit (not depicted here) arranged outside the device, may calculate the two subsections $B_1$=tan $\alpha \times A$ and $B_2$=tan $\beta \times A$. The overall placement width B will subsequently result from adding both subsections $B_1$ and $B_2$.

Figure 8:
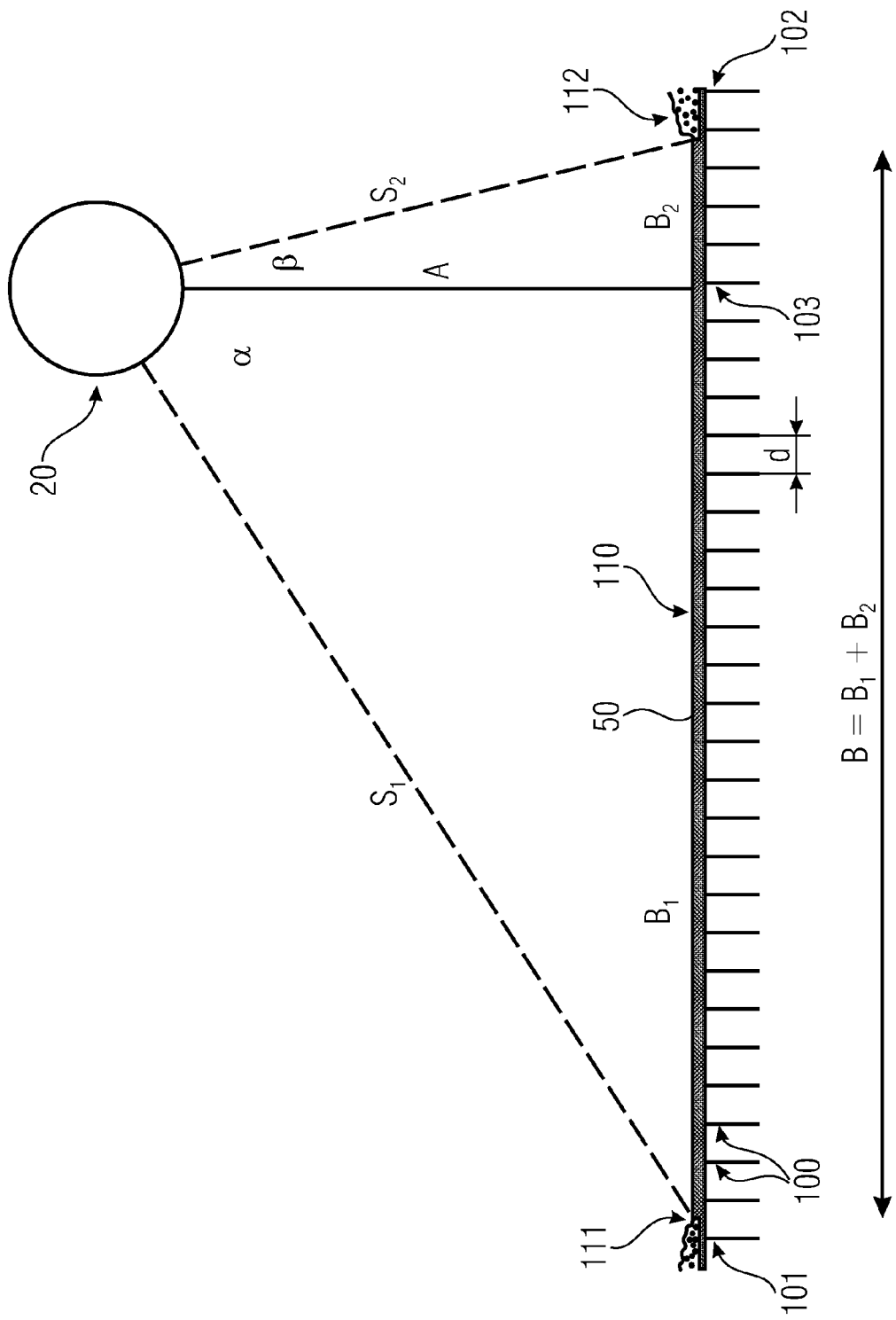
FIG. 8 shows a schematic representation of the mode of operation depicted in FIG. 7, however with a device that is arranged to be offset toward the right in relation to the direction of travel of the construction machine.
Figure 9:
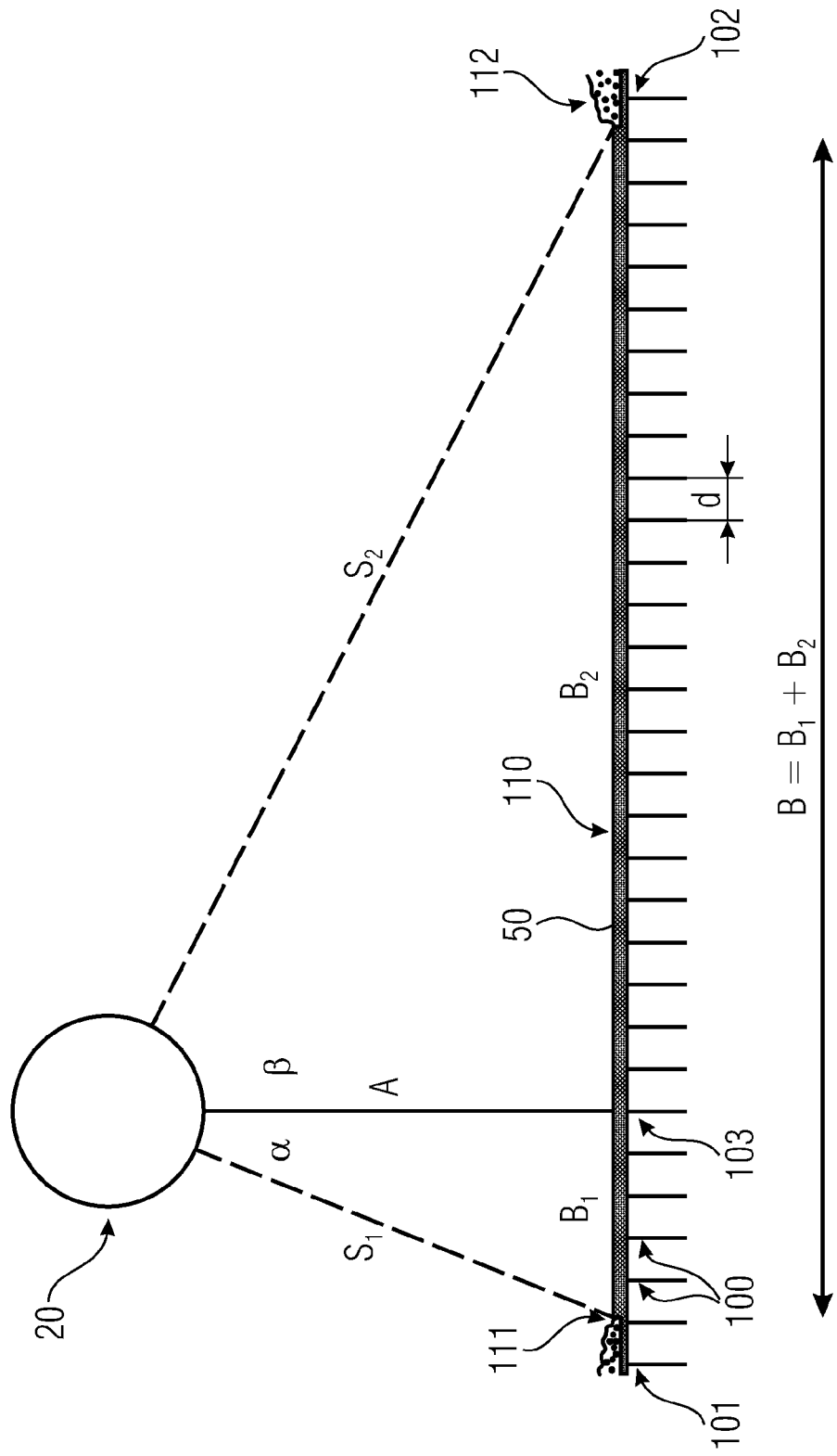
FIG. 9 shows a schematic representation of the mode of operation depicted in FIG. 7, however with a device that is arranged to be offset toward the left in relation to the direction of travel of the construction machine.
Figure 10:
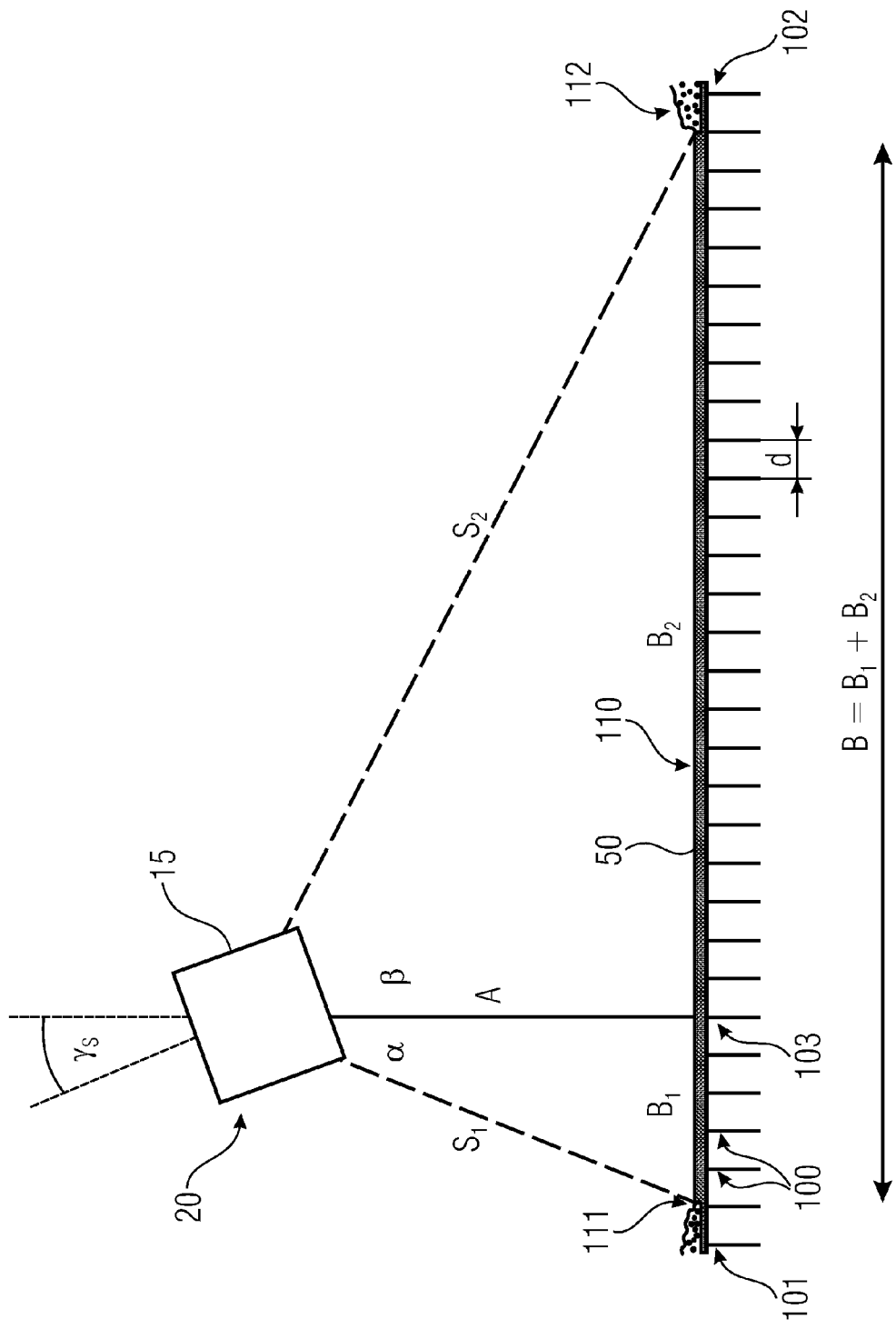
FIG. 10 shows a schematic illustration in accordance with FIG. 9, wherein the device is arranged so as to be twisted by an assembly angle along the scan direction of the infrared temperature measuring head.

Starting from FIG. 7 where the device is arranged to be basically centered transverse to the direction of travel of the construction machine (not shown here), the position 10 of the device at the road finishing machine (not illustrated here) has changed in FIGS. 8, 9 and 10. This means that, in FIG. 8, the device is arranged to be offset to the right relative to the direction of travel of the road finishing machine, whereas, in FIGS. 9 and 10 the device is arranged to the left relative to the direction of travel of the road finishing machine and, additionally, is in a smaller distance A relative to the surface 110 of the newly applied road surface 50. For reasons of simplicity, a steady assembly angle $\gamma_F$ (cf. FIG. 2) of 15°, for example, and an assembly angle $\gamma_S$ of 0° relative to a perpendicular line are assumed in the examples of FIGS. 7 to 10. Thus, the distance A is calculated from A=(h/cos 15).

In the example in accordance with FIG. 7, an overall width of (tan $\alpha_{Max} \times$(h/cos 15))+(tan $\beta_{Max} \times$(h/cos 15))=(tan 60×(4/cos 15))+(tan 60×(4/cos 15))≈14.3 is detected by the infrared temperature measuring head 20 at a maximum overall twisting angle $\alpha_{Max}+\beta_{Max}$ of, for example, about 120° and an assembly height h of the device or the infrared temperature measuring head 20. With a target detection of a newly applied road surface 50 in a placement width B of at least 8 meters, it is thus possible to shift the device at the road finishing machine transverse to its direction of travel by more than 3 meters each, starting from the center of the road finishing machine in the direction of the outer edges 111 and 112 such that the mounted road surface 50 is still detected over its entire width B.

In all the embodiments illustrated in accordance with FIGS. 7 to 10, the surface 110 of the newly applied road surface 50 will be detected by the infrared temperature measuring head 20 over the entire placement width B, even when the overall detection area, due to the large twisting angle of the infrared temperature measuring head 20, is considerably larger than the placement width B and the device, when seen transverse to the direction of travel of the construction machine, is not arranged in the center as is the case in the embodiments in accordance with FIGS. 8 to 10.

In addition, in all the embodiments illustrated in accordance with FIGS. 8 to 10, the controller 40 of the device is effective to control the motor 30 based on the assembly position 10 and the assembly angles $\gamma_F$ and $\gamma_S$ of the device on the construction machine such that the distance d of the measuring points 100 on the surface 110 to be measured remains equal. This is achieved by the fact that the controller 40 or an evaluating unit (not illustrated here) arranged at the device or at the construction machine calculates the angle $\alpha$ and $\beta$ to be set for the infrared temperature measuring head 20 relative to a perpendicular line, i.e. to a measuring point 103, where the infrared temperature measuring head 20 is arranged, in the direction of travel of the construction machine, essentially perpendicularly to the surface 110 of the road building material 50.

In the example of the embodiment in accordance with FIG. 7, the angles $\alpha$ and $\beta$ are equal and each are about 45°, for example. In addition, an assembly height h of the device or the infrared temperature measuring head 20 to the surface 110 of the newly applied road surface 50 of 4 meters, a measuring point distance d to be set of 25 cm and a starting position of the infrared temperature measuring head 20 in the direction of the outer edge 110 are assumed. Thus, the distances $B_1$ and $B_2$ each are $B_1$=$B_2$=(tan $\alpha \times A$)=tan $\alpha \times$(h/cos $\gamma_F$)=tan 45×(4/cos 15)≈3.86 meters to the outer edges 111 and 112.

The first measuring point 100 to be captured in the area of the outer edge 111 is done at a distance of 3.75 meters, starting from a measuring point 103 which represents a so-called zero position for the infrared temperature measuring head 20. Consequently, a first twisting angle $\alpha$=arctan (3.75/(h/cos $\gamma_F$))=arctan(3.75/(4/cos 15))≈arctan 0.91≈42.16° is set for the infrared temperature measuring head 20. For the following measuring point 100 at a distance d=0.25 meters in the direction of the right outer edge 112, a twisting angle of $\alpha$=arctan((3.75−d)/(h/cos $\gamma_F$))=arctan ((3.75−0.25)/(4/cos 15))≈arctan 0.85≈40.20° is to be set. The subsequent twisting angle $\alpha$ is arctan((3.75−2d)/(h/cos $\gamma_F$))=arctan((3.75−0.50)/(4/cos 15))≈arctan 0.78≈38.13°. The other twisting angles $\alpha$ to be set are calculated in analogy.

When approximating the measuring point 103 where the infrared temperature measuring head 20, in the direction of travel of the construction machine, is arranged essentially perpendicularly to the surface 110 of the road building material 50, the twisting angle is $\alpha$=arctan((3.75−14d)/(h/cos $\gamma_F$))=arctan((3.75−3.50)/(4/cos 15))≈arctan 0.06≈3.45°. When reaching the measuring point 103, the twisting angle $\alpha$ to be set consequently is 0°, since the infrared temperature measuring head 20 is again in the so-called zero position. The following twisting angles to be set are calculated in analogy to the calculations performed so far and use the angle $\beta$ for calculation. Consequently, the first twisting angle following after the measuring point 103 and directed in the direction of the right outer edge 112 is $\beta$=arctan((3.75−14d)/(h/cos $\gamma_F$))=arctan((3.75−3.50)/(4/cos 15))≈arctan 0.06≈3.45°. For the following measuring point 100 at a distance d=0.25 meters in the direction of the right outer edge 112, a twisting angle of $\beta=\arctan((3.75-13d)/(h/\cos \gamma_F))=\arctan((3.75-3.25)/(4/\cos 15))\approx\arctan 0.12\approx6.88°$ is to be set. The subsequent twisting angle $\beta$ will then be $((3.75-12d)/(h/\cos \gamma_F))=\arctan((3.75-3.00)/(4/\cos 15))\approx\arctan 0.18\approx10.27°$. The further twisting angles $\beta$ to be set of the infrared temperature measuring head 20 are calculated in analogy.

In FIG. 8, due to the offset position 10 of the device, the angle $\alpha$ of about 60° is considerably larger than the angle $\beta$. The infrared temperature measuring head 20, however, may be twisted by a very large overall angle $(\alpha+\beta)$ of about 120° to 130°, for example. However, in order to ensure a measuring precision of +/−3° C., it is advantageous for the infrared temperature measuring head 20 not to be twisted beyond a maximum value of the two angles $\alpha$ and $\beta$ of about 60° each relative to the, in the direction of movement of the construction machine, perpendicular distance line A. Nevertheless, with a positioning 10 of the device in accordance with FIG. 8, i.e., for example, with an assembly height h of the device in the area of about 4 meters above the surface 110 of the newly applied road building material 50 and a lateral distance $B_2$ to the outer edge 112 of about 1 meter, an overall placement width $B=B_1+B_2=(\tan \alpha \times A)+1=(\tan \alpha \times (h/\cos 15))+1=(\tan 60\times(4/\cos 15))+1\approx7.1+1\approx8.1$ meters can be detected. If the device is, relative to the direction of travel of the road finishing machine, arranged perpendicularly to the surface 110 at the road finishing machine, i.e. the assembly angle $\gamma_F=0°$ relative to the surface 110, the distance A of about 4 meters, in the present example, equals the assembly height h of the device above the surface 110.

With the example in accordance with FIG. 8, the first measuring point 100 to be captured in the area of the outer edge 111 is at a distance of 7.00 meters starting from the measuring point 103 which represents the zero position mentioned already for the infrared temperature measuring head 20. Consequently, a first twisting angle $\alpha=\arctan(7.00/(h/\cos \gamma_F))=\arctan(7.00/(4/\cos 15))\approx\arctan 1.69\approx59.4°$ is set for the infrared temperature measuring head 20. For the following measuring point 100 at a distance d=0.25 meters in the direction of the right outer edge 112, a twisting angle of $\alpha=\arctan((7.00-d)/(h/\cos \gamma_F))=\arctan((7.00-0.25)/(4/\cos 15))\approx\arctan 1.63\approx58.47°$ is to be set. The subsequent twisting angle $\alpha$ will then be $\arctan((7.00-2d)/(h/\cos \gamma_F))=\arctan((7.00-0.50)/(4/\cos 15))\approx\arctan 1.57\approx57.5°$. The further twisting angles a to be set are calculated in analogy.

When approximating the measuring point 103 where the infrared temperature measuring head 20 is, in the direction of travel of the construction machine, arranged essentially perpendicularly to the surface 110 of the road building material 50, the twisting angle is $\alpha=\arctan((7.00-27d)/(h/\cos \gamma_F))=\arctan((7.00-6.75)/(4/\cos 15))\approx\arctan 0.06\approx3.45°$, in analogy to the example of the embodiment in accordance with FIG. 7. When reaching the measuring point 103, the twisting angle a to be set consequently is 0°, since infrared temperature measuring head 20 will then again be in the zero position mentioned already. The subsequent twisting angles to be set are calculated in analogy to the example of the embodiment in accordance with FIG. 7. Consequently, the first twisting angle $\beta$ following after the measuring point 103 in the direction of the right outer edge 112 is $\beta\approx3.45°$. For the following measuring point 100 at a distance d=0.25 meters in the direction of the right outer edge 112, a twisting angle of $\beta\approx6.88°$ is to be set. The next twisting angle $\beta$ is $\approx10.27°$. The further twisting angles $\beta$ to be set of the infrared temperature measuring head 20 are calculated in analogy.

In contrast to FIG. 8, in FIG. 9 the angle $\beta$ of about 60° is essentially larger than the angle $\alpha$. In addition, the assembly height h and, thus, the distance A of the device or the infrared temperature measuring head 20 to the surface 110 of the newly applied road surface 50 is smaller. Exemplarily, the assembly height h is about 3.5 meters. When assuming a lateral distance $B_1$ to the outer edge 111 of 2 meters, with this positioning 10 of the device, it is also possible to detect an overall placement width $B=B_1+B_2=2+(\tan \beta \times A)=2+(\tan \beta \times (h/\cos 15))=2+(\tan 60\times(3.5/\cos_{15}))\approx8.2$ meters. With this example, too, the distance A of about 3.5 meters equals the assembly height h of the device above the surface 110, if the device is, relative to the direction of travel of the road finishing machine, arranged at the road finishing machine to be perpendicular to the surface 110, i.e. the assembly angle $\gamma_F=0°$ relative to the surface 110.

With the example in accordance with FIG. 9, the first measuring point 100 to be captured in the area of the outer edge 111 is at a distance $B_1$ of 2.00 meters starting from the measuring point 103 which represents the zero position mentioned already for the infrared temperature measuring head 20. Consequently, a first twisting angle $\alpha=\arctan(2.00/(h/\cos \gamma_F))=\arctan(2.00/(3.5/\cos 15))\approx\arctan 0.55\approx28.9°$ is set for the infrared temperature measuring head 20. For the following measuring point 100 at a distance d=0.25 meters in the direction of the right outer edge 112, a twisting angle of $\alpha=\arctan((2.00-d)/(h/\cos \gamma_F))=\arctan((2.00-0.25)/(3.5/\cos 15))\approx\arctan 0.48\approx25.78°$ is to be set. The next twisting angle $\alpha$ will then be $\arctan((2.00-2d)/(h/\cos \gamma_F))=\arctan((2.00-0.50)/(3.5/\cos 15))\approx\arctan 0.41\approx22.49°$. The further twisting angles $\alpha$ to be set are calculated in analogy.

When approximating the measuring point 103 where the infrared temperature measuring head 20 is, in the direction of travel of the construction machine, arranged to be essentially perpendicular to the surface 110 of the road finishing machine 50, the twisting angle $\alpha=\arctan((2.00-7d)/(h/\cos \gamma_F))=\arctan((2.00-1.75)/(3.5/\cos 15))\approx\arctan 0.07\approx3.95°$. When reaching the measuring point 103, the twisting angle $\alpha$ to be set consequently is 0° since the infrared temperature measuring head 20 will then again be in the zero position mentioned already. The following twisting angles to be set are calculated in analogy to the example of the embodiment in accordance with FIGS. 7 and 8, however, with an assembly height h=3.5 meters. Thus, the first twisting angle $\beta$ following after the measuring point 103 in the direction of the right outer edge 112 is $\beta\approx3.95°$. For the following measuring point 100 at a distance d=0.25 meters in the direction of the right outer edge 112, a twisting angle of $\beta\approx7.86°$ is to be set. The following twisting angle $\beta$ will then be $\approx11.69°$. The further twisting angles $\beta$ to be set of the infrared temperature measuring head 20 are calculated in analogy.

FIG. 10 basically shows the device arranged at the road finishing machine in accordance with FIG. 9, wherein the device in FIG. 10 is arranged to be twisted by an assembly angle $\gamma_S$ in the range of about 15° in the scan direction of the infrared temperature measuring head 20. Such twisting is usually due to reasons related to assembly which, however, need not necessarily be used for detecting the overall placement width B of the newly applied road surface 50 and has no influence on the operating behavior of the device itself, nor on the infrared temperature measuring head 20.

As far as the controller of the motor 30 which twists the infrared temperature measuring head 20 transverse to the direction of travel of the construction machine is concerned, the calculations are done in analogy to that of FIG. 9, wherein the assembly angle $\gamma_S$ is taken into consideration in the calculation. Thus, the first measuring point 100 to be captured in the area of the outer edge 111 is also at a distance $B_1$ of 2.00 meters starting from the measuring point 103 which represents the zero position mentioned already for the infrared temperature measuring head 20. Consequently, a first twisting angle $\alpha+\gamma_S=\arctan(2.00/(h/\cos \gamma_F))+\gamma_S=\arctan(2.00/(3.5/\cos 15))+15\approx\arctan 0.55+15\approx43.9°$ is set for the infrared temperature measuring head 20. For the following measuring point 100 at a distance d=0.25 meters in the direction of the right outer edge 112, a twisting angle of $\alpha+\gamma_S=\arctan((2.00-d)/(h/\cos \gamma_F))+\gamma_S=\arctan((2.00-0.25)/(3.5/\cos 15))+15\approx\arctan 0.48+15\approx40.78°$ is to be set. The subsequent twisting angle $\alpha+\gamma_S$ will then be $\arctan((2.00-2d)/(h/\cos \gamma_F))+\gamma_S=\arctan ((2.00-0.50)/(3.5/\cos 15))+15\approx\arctan 0.41+15\approx37.49°$. The further twisting angles $\alpha+\gamma_S$ to be set are calculated in analogy.

When approximating the measuring point 103 where the infrared temperature measuring head 20 is, in the direction of travel of the construction machine, arranged to be essentially perpendicularly to the surface 110 of the road building material 50, the twisting angle is $\alpha+\gamma_S=\arctan((2.00-7d)/(h/\cos \gamma_F))+\gamma_S=\arctan((2.00-1.75)/(3.5/\cos 15))+15\approx\arctan 0.07\approx18.95°$. When reaching the measuring point 103, the twisting angle $\alpha+\gamma_S$ to be set will consequently be 15°, since the infrared temperature measuring head 20 will then again be in the zero position mentioned already. The following twisting angles to be set are calculated also in analogy to the embodiment in accordance with FIG. 9, however, taking into consideration the assembly angle $\gamma_S$ as well. Thus, the first twisting angle following after the measuring point 103 in the direction of the right outer edge 112 is $\beta-\gamma_S\approx-11.05°$. For the following measuring point 100 at a distance d=0.25 meters in the direction of the right outer edge 112, a twisting angle of $\beta-\gamma_S\approx-7.14°$ is to be set. The following twisting angle $\beta-\gamma_S$ will then be $\approx-3.31°$.

Figure 11:
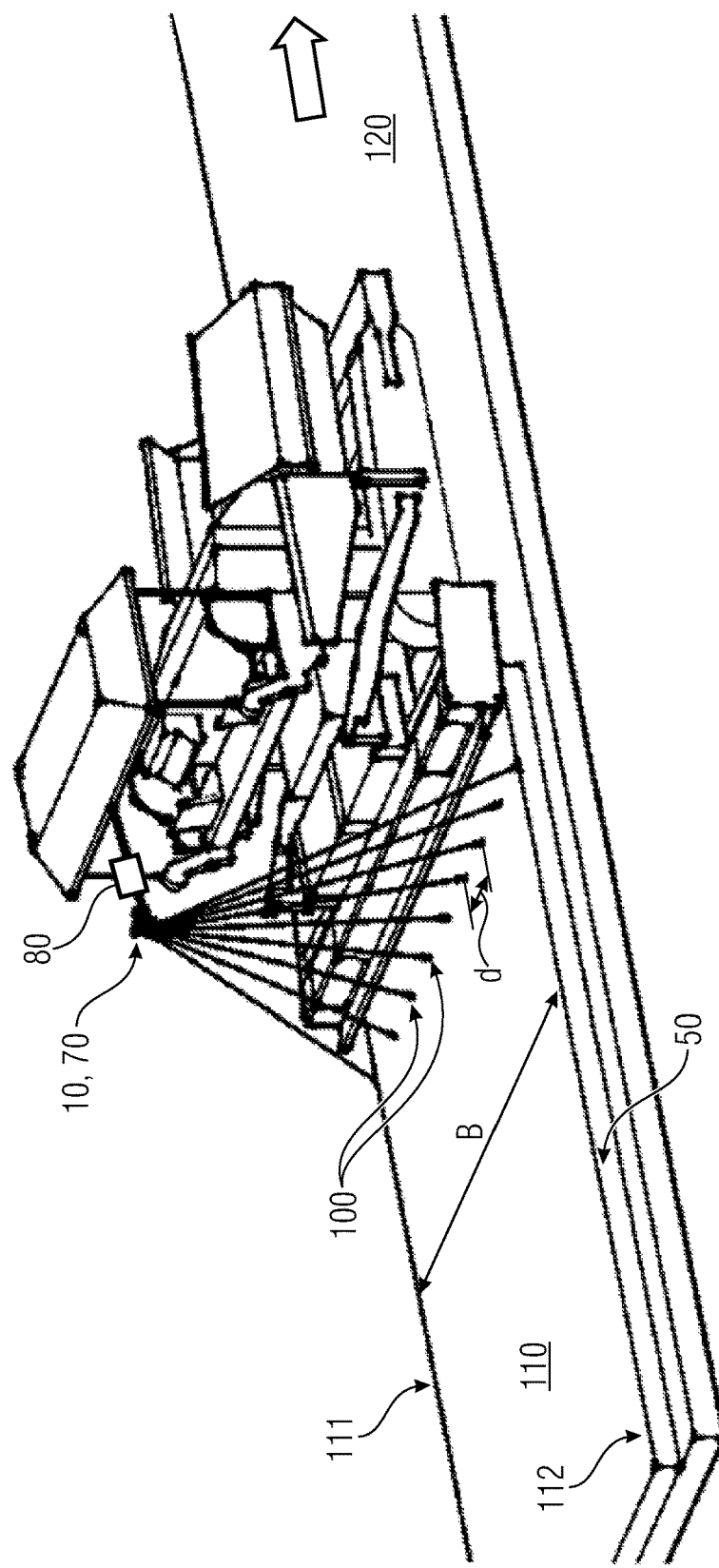
FIG. 11 shows a schematic illustration of a road finishing machine comprising an inventive device arranged at the back end thereof.

The road finishing machine schematically illustrated in FIG. 11 comprises the inventive device at its back end at the position 10. The direction of travel of the road finishing machine is illustrated by an arrow on the ground 120. A distance measurer 70, for example a laser distance measurer, and a weather station 80, which exemplarily determines the wind speed and the ambient temperature in the area of the road finishing machine, are also arranged in the area of the inventive device. The inventive device measures the temperature of the surface 110 of the newly applied road surface 50 over the placement width B which is limited laterally, i.e. transverse to the direction of travel of the road finishing machine, by the outer edges 111 and 112. Thus, the measuring values are captured at the measuring points 100 illustrated schematically and arranged in equal distances d transverse to the direction of travel of the road finishing machine. When the road finishing machine moves in the direction of travel, the scan movement of the infrared temperature measuring head 20 results in measuring points 100 on a line of a series of measurements which, when observed in reality, is diagonal. In this context, it is to be mentioned that the illustration of the points in FIGS. 11 and 12 is purely schematic and only serves to understand the mode of operation of the device.

Figure 12:
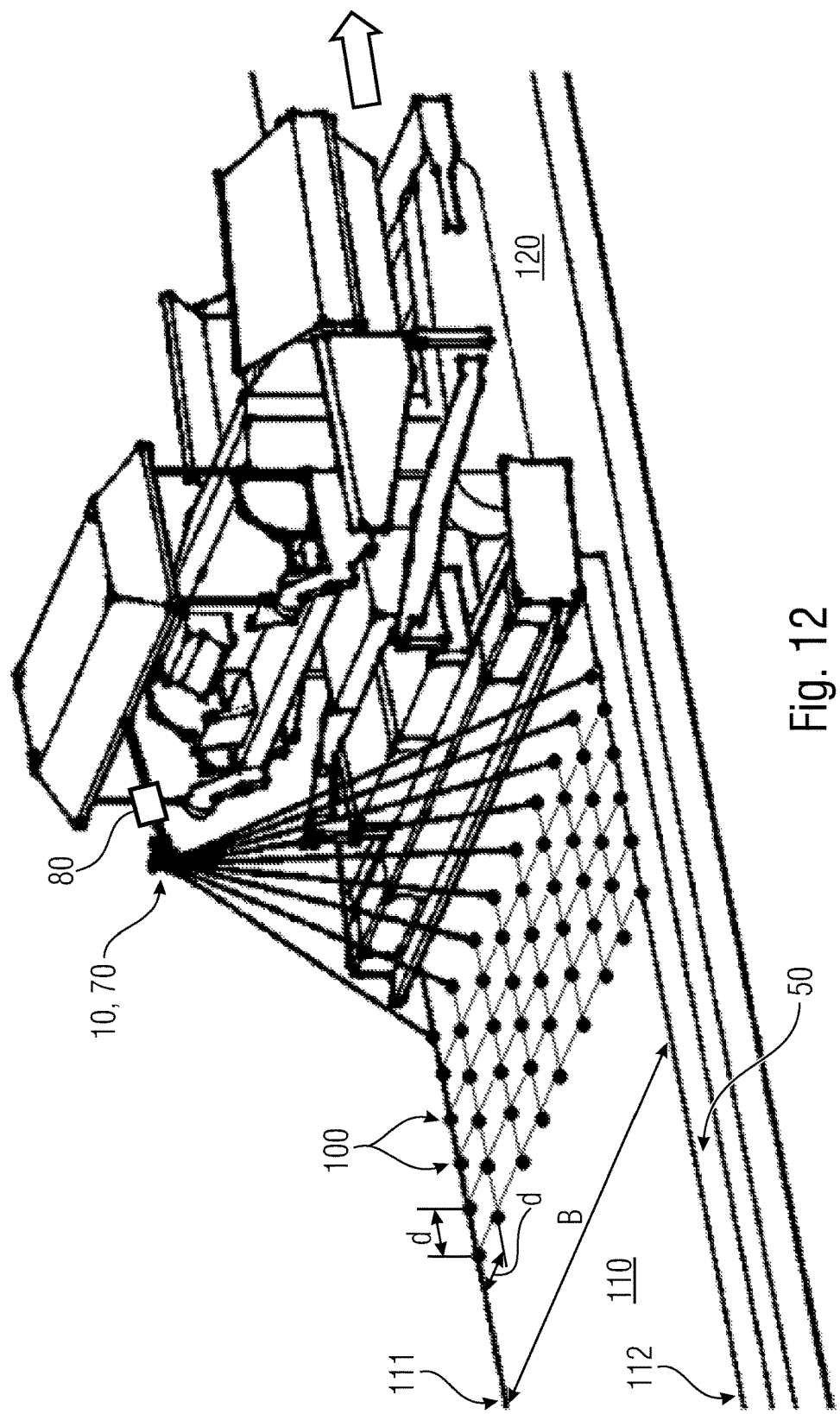
FIG. 12 shows a schematic illustration of the road finishing machine illustrated in FIG. 11 and comprising a measuring point pattern illustrated schematically on the surface of the newly applied road building material.

FIG. 12 basically shows the road finishing machine of FIG. 11, however, with a measuring point pattern illustrated schematically on the surface 110 of the newly applied road building material 50 and directly behind the asphalt plank. The measuring points 100 thus exhibit equal distances d relative to one another both transverse to the direction of travel of the construction machine and in the direction of travel of the construction machine such that a steady measuring point pattern results behind the asphalt plank over the entire placement width B of the newly applied road building material 50.

It shall be pointed out here that the inventive approach of the variable measuring times that was explained by means of FIGS. 3 to 6 may also be employed in an arrangement of the device in accordance with FIGS. 9 and 10. Moreover, the inventive approach of the variable measuring times may also be employed in combination with the approach, explained by means of FIGS. 7 to 9, of maintaining constant distances of the measuring points.

Even though some aspects have been described within the context of a device, it is understood that said aspects also represent a description of the corresponding method, so that a block or a structural component of a device is also to be understood as a corresponding method step or as a feature of a method step. By analogy therewith, aspects that have been described within the context of or as a method step also represent a description of a corresponding block or detail or feature of a corresponding device.

While this invention has been described in terms of several embodiments, there are alterations, permutations, and equivalents which fall within the scope of this invention. It should also be noted that there are many alternative ways of implementing the methods and compositions of the present invention. It is therefore intended that the following appended claims be interpreted as including all such alterations, permutations and equivalents as fall within the true spirit and scope of the present invention.

The invention claimed is:

1. A device for determining a temperature of a road building material applied by a construction machine in a placement width, comprising:
   an infrared temperature measuring head,
   a motor, and
   a controller,
   wherein the infrared temperature measuring head is arranged to be twistable, by the motor, in a manner transverse to a direction of travel of the construction machine to scan a surface of the road building material so as to capture temperature measuring values of the surface of the road building material during a rotational movement at a plurality of measuring points spaced apart from one another,
   wherein
   the controller is configured to vary a scanning speed as a function of a position of the measuring point.

2. The device as claimed in claim 1, wherein the controller is configured to set the scanning speed as a function of an angle by which the infrared temperature measuring head is twisted in relation to a perpendicular to the surface.

3. The device as claimed in claim 2, wherein the controller is configured to reduce the scanning speed as the angle increases, and to increase the scanning speed as the angle decreases.

4. The device as claimed in claim 2, wherein the scanning speed is higher, within a first angular range around the perpendicular to the surface, than is the scanning speed within a second angular range outside the first angular range.

5. The device as claimed in claim 2, wherein the scanning speed within a first angular range around the perpendicular to the surface comprises a first value, and wherein the scanning speed within a second angular range and within a third angular range, which span the first angular range and a first and/or second edge of the surface, comprises a second value lower than the first value.

6. The device as claimed in claim 1, wherein the controller is configured to control the motor such that the infrared temperature measuring head is oriented toward a measuring point in order to capture a temperature measuring value of said measuring point during a dwell time, the controller being configured to set the dwell time as a function of a position of the measuring point along the width of the surface.

7. The device as claimed in claim 1, wherein the controller is effective to control, when assembling the device on the construction machine in an area within the placement width, the motor based on the assembly position of the device on the construction machine such that the distance between measuring points on the surface to be measured remains equal.

8. The device as claimed in claim 7, wherein the controller is effective to control the motor additionally based on assembly angles of the device on the construction machine.

9. The device as claimed in claim 1, wherein the controller is effective to change a speed of movement of the infrared temperature measuring head as a function of the speed of travel of the construction machine.

10. The device as claimed in claim 1, wherein the controller is effective to change the direction of movement of the infrared temperature measuring head as soon as the measured temperature falls below a predetermined minimum value at at least one measuring point.

11. The device as claimed in claim 10, wherein the position where the infrared temperature measuring head changes its direction of movement is stored in the controller or in an evaluating unit arranged at the device or at the construction machine for calculating the placement width of the newly applied road building material.

12. The device as claimed in claim 1, wherein the distance of the measuring points and/or the duration of the temperature measurement at a measuring point is/are settable.

13. The device as claimed in claim 1, wherein the device comprises a contactless distance measurer which is effective to measure a distance of the infrared temperature measuring head to the measuring point where the infrared temperature measuring head is directed to the surface of the road building material essentially perpendicularly.

14. The device as claimed in claim 13, wherein the contactless distance measurer is electrically connected to the controller.

15. The device as claimed in claim 1, wherein the controller is connectable electrically to a weather station arranged at the construction machine which determines a wind speed, ambient temperature, air humidity, rainfall and/or another ambient parameter in the area of the construction machine.

16. The device as claimed in claim 1, wherein the motor is a stepper motor, a servomotor, a direct-current motor or a direct-current motor comprising a gear unit.

17. A construction machine comprising at least one device for determining a temperature of a road building material applied by a construction machine in a placement width, said device comprising:
an infrared temperature measuring head,
a motor, and
a controller,
wherein the infrared temperature measuring head is arranged to be twistable, by the motor, in a manner transverse to a direction of travel of the construction machine to scan a surface of the road building material so as to capture temperature measuring values of the surface of the road building material during a rotational movement at a plurality of measuring points spaced apart from one another,
wherein
the controller is configured to vary a scanning speed as a function of a position of the measuring point,
said device being arranged in a back area and/or in a front area of the construction machine.

18. A method of determining a temperature of a road building material applied by a construction machine in a placement width, the method comprising:
scanning a surface of the road building material by twisting an infrared temperature measuring head in a direction transverse to a direction of travel of the construction machine, and
capturing, by the infrared temperature measuring head, temperature measuring values of the surface of the road building material at a plurality of measuring points spaced apart from one another,
wherein
a scanning speed at which the infrared temperature measuring head scans a measuring point is variable as a function of a position of the measuring point.

* * * * *